US007396341B2

(12) United States Patent
Schyra et al.

(10) Patent No.: US 7,396,341 B2
(45) Date of Patent: Jul. 8, 2008

(54) BLOCKING DEVICE FOR A LOCKING STRESSING MECHANISM HAVING A SPRING-ACTUATED OUTPUT DRIVE DEVICE

(75) Inventors: Michael Schyra, Wuppertal (DE); Herbert Wachtel, Bingen (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 1140 days.

(21) Appl. No.: 10/650,869

(22) Filed: Aug. 27, 2003

(65) Prior Publication Data

US 2004/0094147 A1 May 20, 2004

Related U.S. Application Data

(60) Provisional application No. 60/458,212, filed on Mar. 27, 2003.

(30) Foreign Application Priority Data

Aug. 28, 2002 (DE) ................................ 102 39 443

(51) Int. Cl.
*A61M 31/00* (2006.01)

(52) U.S. Cl. ............... 604/92; 128/203.15; 128/203.12; 604/82; 604/48

(58) Field of Classification Search ................. 604/192, 604/92; 221/151, 265, 222, 237, 203, 204, 221/154, 152, 2, 6, 7; 70/278.7; 116/240, 116/241, 281, 288, 294, 319, 321, 324
See application file for complete search history.

(56) References Cited

U.S. PATENT DOCUMENTS 5,263,475 A * 11/1993 Altermatt et al. ....... 128/203.15

5,740,792 A * 4/1998 Ashley et al. .......... 128/203.15
5,829,434 A * 11/1998 Ambrosio et al. ...... 128/203.15

(Continued)

FOREIGN PATENT DOCUMENTS

WO WO 93 21980 A 11/1993

(Continued)

*Primary Examiner*—Terrell Mckinnon
*Assistant Examiner*—Ian K Holloway
(74) *Attorney, Agent, or Firm*—David A. Dow; Michael P. Morris; Mary-Ellen M. Devlin

(57) ABSTRACT

A locking-stressing-mechanism with spring-actuated output drive and a counter with which an apparatus of this kind is fitted, accommodated in a two part housing the two parts of which are mounted to be rotatable relative to each other, can be blocked by means of a pre-stressed leaf spring. The leaf spring is initially accommodated in a recess in the wall of one housing part. As soon as the permitted number of actuations has been reached a push rod pushes the leaf spring out of its resting position. The leaf spring then jumps into a recess in the wall of the other housing part and the two housing parts can no longer be rotated relative to each other. The push rod may be mounted on the pointer of the counter. This blocking device can only be overcome by the application of a force which is sufficient to destroy the device. The device is suitable for blocking a high pressure atomiser or a needleless injector with which a fluid is atomised to form an aerosol or a fluid is injected into a biological tissue.

11 Claims, 2 Drawing Sheets

U.S. PATENT DOCUMENTS

| | | | | |
|---|---|---|---|---|
| 5,871,007 | A * | 2/1999 | Clark, Jr. | 128/200.23 |
| 5,988,496 | A * | 11/1999 | Bruna | 235/91 R |
| 6,065,471 | A * | 5/2000 | Schaeffer et al. | 128/203.15 |
| 6,453,795 | B1 * | 9/2002 | Eicher et al. | 92/23 |
| 6,729,330 | B2 * | 5/2004 | Scarrott et al. | 128/205.23 |
| 6,948,495 | B2 * | 9/2005 | Seppala | 128/203.15 |
| 2006/0285987 | A1 * | 12/2006 | Jaeger et al. | 417/572 |

FOREIGN PATENT DOCUMENTS

| | | |
|---|---|---|
| WO | WO 95 34874 A | 12/1995 |
| WO | WO 97 12687 | 4/1997 |
| WO | WO 97 24586 A | 7/1997 |

* cited by examiner

BLOCKING DEVICE FOR A LOCKING STRESSING MECHANISM HAVING A SPRING-ACTUATED OUTPUT DRIVE DEVICE

The priority benefit of DE 10239443.1, filed Aug. 28, 2002 and U.S. Provisional Application No. 60/458,212, filed Mar. 27, 2003 are hereby claimed, both of which are incorporated by reference herein.

FIELD OF THE INVENTION

The invention relates to a blocking device by means of which the proper use of a device equipped with a locking-stressing mechanism and a spring-actuated output drive is prevented after a given number of actuations. The device may be, for example, a high pressure atomiser or a needleless injector.

BACKGROUND AND DESCRIPTION OF THE INVENTION

The aim of the invention is to reliably limit the period of use of such a device and meet safety requirements. The reasons for the limitation may be based on hygiene, medical or technical considerations.

The locking-stressing-mechanism, which is to be blocked after the permitted period of use has elapsed preferably comprises a helical thrust gear accommodated in a manually operated device, by means of which a rotary movement is converted into a linear movement and an operating spring is put under tension. The operating spring acts on a spring component of the locking-stressing-mechanism the movement of which is initially blocked as soon as the operating spring has reached the tensioned state. Secured in the spring component there may be a piston movably mounted in a cylinder. Inside the cylinder, in front of the piston, is a liquid which is expelled out through a nozzle as the locking mechanism of the locking-stressing mechanism is actuated by the piston driven by the operating spring. The number of actuations of the locking-stressing-mechanism and hence of the device can be counted by a mechanical counter.

WO-93/21980 describes a metered-dose inhaler. The dose of a substance to be inhaled is introduced, by means of a hand-operated device, from a supply of the substance contained in the inhaler, into a chamber from which the dose is expelled with the current of air which the user sucks in through the inhaler as they breathe in. The metered-dose inhaler is fitted with a counter which comprises a rotatable screw spindle and a rod, one end of which engages in the form of a nose in the thread of the screw spindle. The rod moves parallel to the screw spindle as the rotation of the spindle increases. The counter indicates, by means of the position of the nose-like end of the rod, the number of doses which have already been taken out of the supply of substance, or those which can still be taken out. The other end of the rod is movably held in a guide shaft into which the rod extends more deeply as the rotation of the screw spindle increases. As soon as the supply of substance in the inhaler is coming to an end, the nose-like end of the rod engaging in the screw spindle reaches that part of the spindle which has a number of courses of thread having a greater pitch than the rest of the screw spindle. As a result, on each rotation of the screw spindle, the rod moves along faster than before. The other end of the rod meanwhile bears on a flexible lever, and further actuation of the metered-dose inhaler is prevented.

WO-97/20590 describes a locking stressing mechanism for a spring-actuated output drive. WO-97/24586 describes a mechanical counter for a metering device. WO-97/12687 describes a device for generating high pressure in a fluid in a miniature arrangement provided with a locking stressing mechanism and a counter. The apparatus is used to atomise a fluid to produce an inhalable aerosol. WO-01/64268 describes a needleless injector which contains a locking stressing mechanism.

The pieces of equipment mentioned above by way of example are intended for repeated use, e.g. for repeated atomisation of a given amount of liquid to produce an aerosol for inhalation into the lungs, or for needleless injection of a given quantity of liquid underneath the skin of humans or animals. The quantity of liquid atomised or injected may contain a therapeutically active substance.

An object of the present invention is to provide a device for an apparatus which will reliably, effectively and finally prevent further use of the apparatus after a given number of actuations if there is a compelling reason for this. The apparatus comprises a locking-stressing-mechanism with an operating spring and a spring transfer member in which is accommodated a piston which is mounted to be movable in a cylinder. The components are housed in a two-part housing which comprises an upper housing part and a lower housing part. The two housing parts are mounted to be rotatable relative to each other. The operating spring is tensioned by means of a screw thrust gear by manually rotating the two housing parts relative to each other. At the same time as the housing parts are rotated relative to each other, a mechanical counter is actuated which comprises a threaded spindle and a slider. The threaded spindle is mounted in the wall of the lower housing part. The slider is moved up or down the spindle by an amount which depends on the number of rotations of the two housing parts relative to each other.

This problem is solved according to the invention by a device having the following characterising features:

A recess is provided in the outer wall of the lower housing part and in the inner wall of the upper housing part. The two recesses are opposite each other when the two housing parts are in a given rotary position.

In the recess in the lower housing part there is a movable blocking element which is located only in this recess before the blocking device is activated and allows the two housing parts to rotate relative to each other. After the activation of the blocking device the blocking element is located in both recesses and prevents the two housing parts from rotating relative to each other.

By means of a push-rod which co-operates with the slider on the spindle of the counter, the blocking element is moved out of its resting position into the position which it occupies after activation of the blocking device.

On the one hand, the push-rod may be mounted on the slider to the side of the spindle of the counter. In this embodiment of the blocking device, during normal use of the device, the slider moves towards the upper spindle mounting and towards the upper housing part. The recess in the wall of the lower housing part is mounted next to the axis of the counter spindle. Before the slider makes contact with the upper spindle mounting, the push-rod moves the blocking element located in the recess in the wall of the lower housing part out of its resting position and thereby activates the blocking device.

The push-rod can also be constructed as an extension of the blocking element. In this embodiment, the end of the push-rod projects into the path travelled by the slider during normal use of the device before the slider comes to abut on the upper mounting of the counter spindle. This embodiment works in exactly the same way as the embodiment described above.

In another embodiment of the blocking device the push rod may be constructed as an extension of the counter spindle and may project beyond the upper spindle mounting. In this case the counter spindle is mounted to be axially moveable. The recess in the wall of the lower housing part is preferably provided on the axis of the counter spindle. Before the blocking device is activated the counter spindle is pressed against the lower spindle mounting by a spring, e.g. a helical spring. In this embodiment of the blocking device the slider moves towards the lower spindle mounting during normal use of the device. As soon as the slider comes to abut on the lower spindle mounting, the counter spindle moves axially towards the upper housing part as it continues to rotate. The extension of the counter spindle in the form of a push rod moves the blocking element located in the recess in the wall of the lower housing part out of its resting position, thereby activating the blocking device.

In a reversal of the embodiments described, the blocking element may be pulled out of its resting position by the slider.

The blocking element located in the wall of the lower housing part may be axially or radially moveable. The blocking element may be a leaf spring, preferably a pre-stressed leaf spring with two legs preferably made of metal.

The blocking device according to the invention has the following advantages:

It is suitable for miniaturised equipment.

It is arranged between the housing parts which overlap one another and in its position of use in a device it is inaccessible to the user.

It is easy to assemble.

A blocking element in the form of a pre-stressed leaf spring with two legs is secured against movement in its resting position without any additional effort.

A pre-stressed leaf spring can be pushed into or pulled out of its resting position with relatively little force.

A pre-stressed leaf spring with two legs jumps abruptly from its resting position into the position it occupies when the blocking device is activated, as soon as it has been moved a certain distance by means of a push rod. Thus the response point of the blocking device is precisely fixed.

The rotation of the two housing parts relative to one another is blocked directly as soon as the blocking element, which was originally located in the recess in the wall of the lower housing part, is situated in both recesses at the same time.

The activated blocking device which contains a pre-stressed metal leaf spring can only be overcome by a force moment amounting to several Newton metres, which will destroy the blocked device.

The blocking device according to the invention is used for example in a high pressure atomiser or in a needleless injector. A medical liquid administered using such a device may contain a drug dissolved in a solvent. Suitable solvents include, for example, water, ethanol or mixture thereof. The drugs in question may be, for example, Berotec (fenoterol hydrobromide; 1-(3,5-dihydroxy-phenyl)-2-[[1-(4-hydroxybenzyl)-ethyl]-amino]-ethanol-hydrobromide), Atrovent (ipratropium bromide), Berodual (combination of fenoterol hydrobromide and ipratropium bromide), salbutamol (or albuterol), Combivent, Oxivent (oxitropium bromide), Ba 679 (tiotropium bromide), BEA 2108 (tropenol di-(2-thienyl glycolate), flunisolide, budesonide and others.

DESCRIPTION OF THE PREFERRED EMBODIMENT

Figure 1:
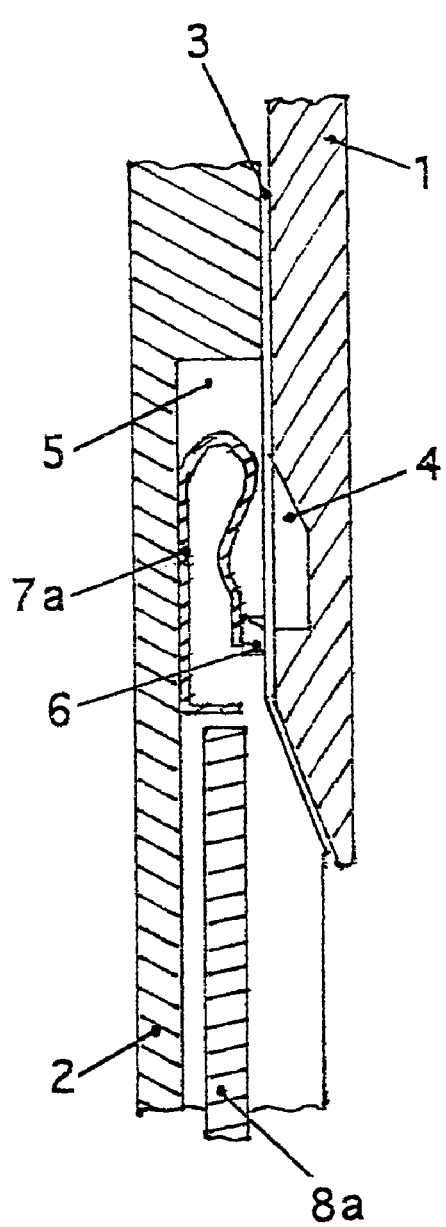
FIG. 1 shows a partial longitudinal section through the wall of the lower and upper housing part of a blocking device in the resting position.
Figure 2:
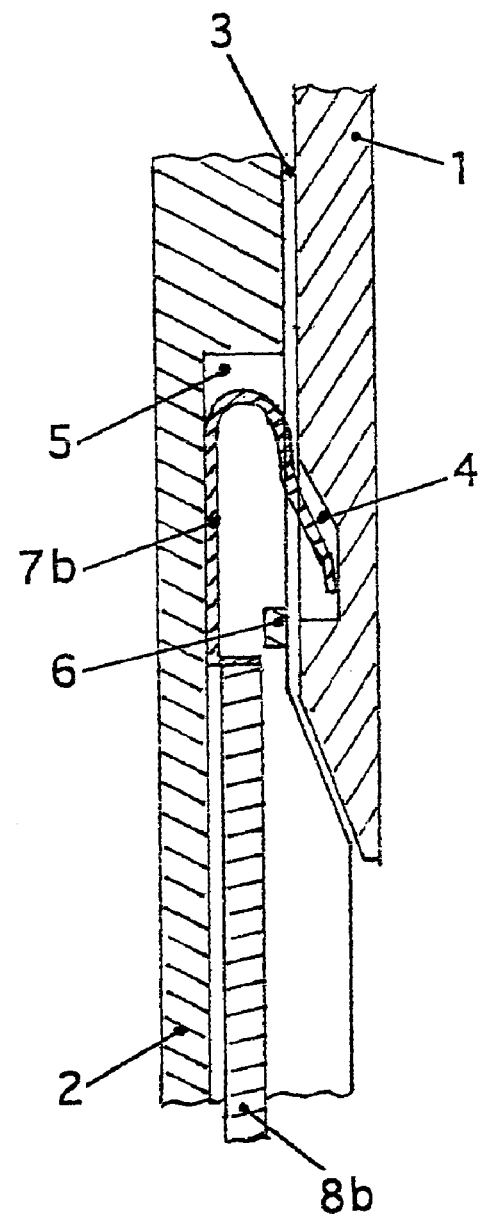
FIG. 2 shows a partial longitudinal section through the wall of an upper housing part of a blocking device in the active position.

A preferred embodiment of the blocking device according to the invention will be explained in more detail with reference to the figures. FIGS. 1 and 2 show partial longitudinal sections through the wall of the lower and upper housing part as well as a leaf spring as a blocking element and a push rod level with the recesses in the walls. The longitudinal section runs parallel to the axis of the lower and upper housing parts.

Figure 3:
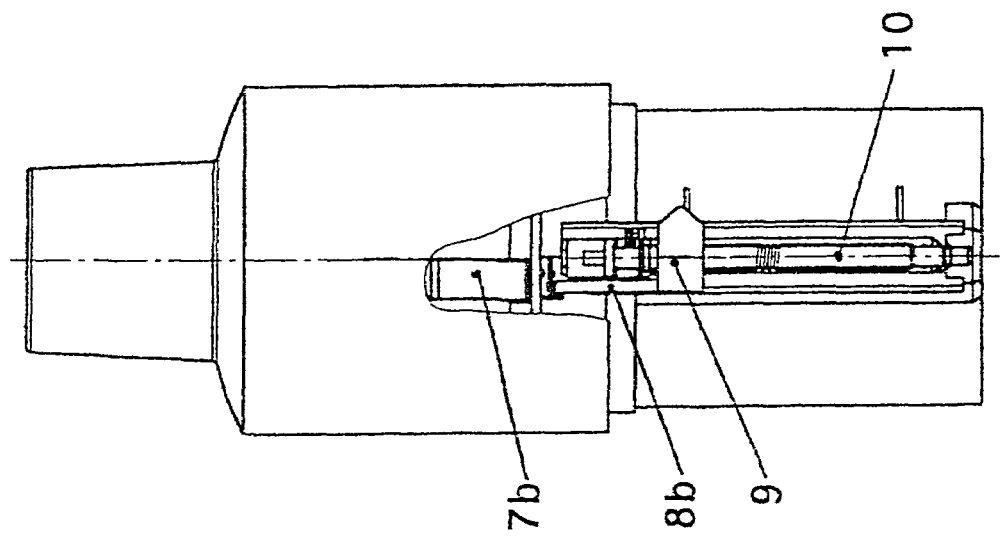
FIG. 3 shows a longitudinal elevation of a blocking device cut open in the region of the counter of the blocking device in the resting position.
Figure 4:
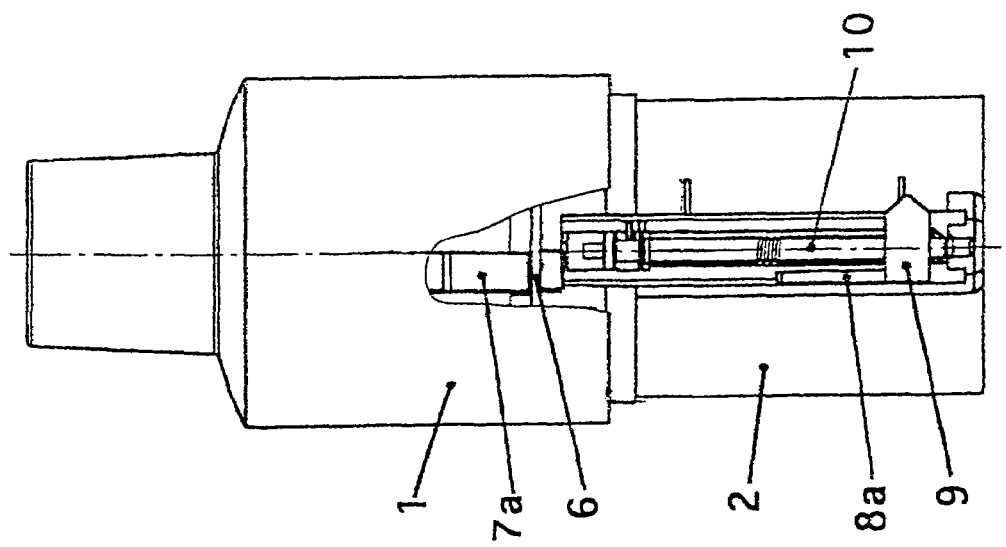
FIG. 4 shows a longitudinal elevation of a device cut open in the region of the counter of the blocking device in the active position.

FIGS. 3 and 4 show a longitudinal elevation of a device cut open in the region of the counter and the blocking device.

In FIGS. 1 and 3 the blocking device is shown in the resting position. The blocking element is in its resting position and is located only in the recess in the wall of the lower housing part. FIGS. 2 and 4 show the blocking device activated. The blocking element has been moved out of its resting position and is located in both recesses in the walls of the two housing parts.

The upper housing part (1) overlaps the lower housing part (2). The gap (3) between the two housing parts, mounted to be rotatable relative to each other, is exaggerated in the drawing. In the upper housing part there is the recess (4) and in the lower housing part the recess (5). The recess (5) contains an undercut projection (6) which is connected to the lower housing part at the side walls of the recess (5). The push rod (8a, 8b) projects into the recess in the wall of the lower housing part. The push rod is mounted on the slider (not shown in FIGS. 1 and 2) which is located on the spindle (not shown in FIGS. 1 and 2) of the counter. The blocking element is a leaf spring with two legs. In its resting position the leaf spring (7a) is jammed between the base of the recess (5) and the undercut projection (6). The push rod (8a) is shown in a position which it occupies shortly before making contact with the leaf spring (7a). As the device is further actuated the push rod moves towards the leaf spring and pushes it out of its resting position, until the end of the leaf spring jumps forward behind the projection (6). If the two recesses (4) and (5) are not yet located opposite each other at this moment the end of the leaf spring which has jumped forward behind the projection (6) first makes contact with the inner wall of the upper housing part. As soon as the two recesses (4) and (5) are located opposite one another, as the rotation of the two housing parts relative to each other continues, the end of the leaf spring jumps into the recess (4). The leaf spring (7b) is thus located in both recesses and the blocking device is activated.

FIG. 3 shows the spindle (10) of the counter on which the slider (9) is located in its (lower) starting position before the device is used for the first time. The push rod (8a) is at some distance from the leaf spring (7a).

In FIG. 4 the slider on the spindle is in its (top) end position in which it has made contact with the end of the leaf spring (8b) and pushed the leaf spring out of its resting position, as a result of which the blocking device has been activated.

The pre-stressed leaf spring (7a; 7b) shown in the figures as a blocking element consists for example of spring steel about 0.2 mm thick and is about 3.5 mm wide. The two recesses in the walls of the two housing parts are about 4 mm wide and about 1 mm deep. Once the blocking device has been activated the two housing parts can only be rotated relative to one another by the application of considerable force (force moment about 3 Newton metres), but this destroys the device and makes it unusable.

What is claimed is:

1. Blocking device for an apparatus which comprises a locking-stressing-mechanism with an operating spring and a spring transfer member in which is accommodated a piston which is mounted to be moveable in a cylinder, and these components are housed in a two part housing which comprises an upper housing part and a lower housing part, said upper housing part having an inner wall and said lower housing part having an outer wall, and the two parts are mounted to be rotatable relative to each other, and said operating spring is tensioned by means of a screw thrust gear by manually rotating said two housing parts relative to each other, and at the same time as said housing parts are rotated relative to each other a mechanical counter is actuated which comprises a threaded spindle and a slider, and said threaded spindle is mounted in said wall of the lower housing part, and said slider is moved along said spindle by an amount which depends on the number of rotations of said two housing parts relative to each other, wherein a recess is provided in said outer wall of said lower housing part and in said inner wall of said upper housing part, and the two recesses are opposite each other when said two housing parts are in a given rotary position, and a moveable blocking element is provided which is located initially only in the recess in said lower housing part and a push rod for moving said blocking element partially into the recess in said upper housing part to prevent the upper and lower housing parts from rotating relative to each other is provided which cooperates with said slider on said spindle of said counter.

2. Blocking device according to claim 1, wherein said push rod is mounted on the slider.

3. Blocking device according to claim 1, wherein said push rod is mounted on the blocking element.

4. Blocking device according to claim 1, wherein said push rod is constructed as an extension of the spindle of the counter and the spindle is mounted to be axially moveable.

5. Blocking device according to claim 1, wherein said blocking element is moveable in the axial direction.

6. Blocking device according to claim 1, wherein said blocking element is a pre-stressed leaf spring.

7. Blocking device according to claim 1, wherein said blocking element is a pre-stressed leaf spring with two legs.

8. Blocking device according to claim 7, wherein said pre-stressed leaf spring is further comprised of metal.

9. Use of a blocking device according to claim 1 for blocking an atomiser for atomising a liquid which contains a pharmaceutically active substance.

10. Use of the blocking device according to claim 1 for blocking a needleless injector for injecting a liquid which contains a pharmaceutical active substance into animal or human tissue.

11. A method for blocking a needleless injector for injecting a liquid which contains a pharmaceutically active substance into animal or human tissue, said method comprised of the use of a blocking device according to claim 1.

* * * * *